United States Patent
Yakubovsky et al.

(10) Patent No.: US 8,237,123 B2
(45) Date of Patent: Aug. 7, 2012

(54) APPARATUS FOR PREVENTING DAMAGE TO RETRACTOR IN ROTATING IMAGING SYSTEM

(75) Inventors: Leonid Yakubovsky, Haifa (IL); Alexander Vaisburd, Haifa (IL)

(73) Assignee: General Electric Company, Schenectady, NY (US)

( * ) Notice: Subject to any disclaimer, the term of this patent is extended or adjusted under 35 U.S.C. 154(b) by 749 days.

(21) Appl. No.: 12/270,617

(22) Filed: Nov. 13, 2008

(65) Prior Publication Data

US 2010/0119043 A1  May 13, 2010

(51) Int. Cl.
*G01T 1/20* (2006.01)
(52) U.S. Cl. .................................... 250/363.02
(58) Field of Classification Search ... 250/361 R–363.1, 250/370.08–370.11; 378/4, 11, 114, 117
See application file for complete search history.

(56) References Cited

U.S. PATENT DOCUMENTS

| | | | |
|---|---|---|---|
| 1,665,715 A * | 4/1928 | Noisom | 33/355 R |
| 2,406,211 A * | 8/1946 | Flint | 33/380 |
| 2,738,491 A * | 3/1956 | Mihalakis | 340/960 |
| 3,289,475 A * | 12/1966 | Kenyon | 73/178 R |
| 4,366,577 A | 12/1982 | Brandt | |
| 4,740,690 A | 4/1988 | Mosier | |
| 5,523,571 A | 6/1996 | Velaquez et al. | |
| 6,097,030 A * | 8/2000 | Tokarski et al. | 250/363.04 |
| 7,573,034 B2 * | 8/2009 | Heath et al. | 250/361 R |
| 2003/0160731 A1 | 8/2003 | Wensink | |
| 2003/0177649 A1 | 9/2003 | Ito et al. | |
| 2005/0259782 A1 | 11/2005 | Kasuya | |
| 2006/0120513 A1 * | 6/2006 | Buttner et al. | 378/206 |
| 2006/0202650 A1 | 9/2006 | Hausner et al. | |
| 2006/0241408 A1 * | 10/2006 | Yakubovsky et al. | 600/429 |
| 2006/0285641 A1 | 12/2006 | Scherch | |
| 2007/0183566 A1 | 8/2007 | Tsujita et al. | |
| 2008/0267352 A1 | 10/2008 | Aoi et al. | |
| 2010/0121604 A1 | 5/2010 | Vaisburd | |

OTHER PUBLICATIONS

Data Sheet for Bourns 3590—Precision Potentiometer, RoHS Directive 2002/95/EC Jan. 27, 2003 including Annex, (2) pages.
Technical Data Sheet for Tilt sensor example, Freescale Semiconductor, Inc., Document Number: MMA7450L, Rev. 2, Jul. 2007, (1) page.
E-Chain product overview, http://www.igus.com/echain.asp, igus inc.—E-Chain cable carrier for automated machinery, (7) pages.
LeviChain Energy Chain Systems, LeviChain—magnetically suspended cable carrier, http://www.igus.com/levichain.asp, (2) pages.
Energy Chain Systems "Zipper"—Zipper Chain for fast installation, http://www.igus.com/show_zip2.asp, (3) pages.

* cited by examiner

*Primary Examiner* — David Porta
*Assistant Examiner* — Casey Bryant
(74) *Attorney, Agent, or Firm* — The Small Patent Law Group; Dean D. Small (57) ABSTRACT

A rotating imaging system has a rotating portion that is configured to rotate about a central axis. A tilt gauge has a housing mounted to the rotating portion and a gravity influenced flag with a free end configured to move separately with respect to the housing. The tilt gauge is configured to provide a visual indication of a rotational position of the rotating portion.

21 Claims, 10 Drawing Sheets

APPARATUS FOR PREVENTING DAMAGE TO RETRACTOR IN ROTATING IMAGING SYSTEM

BACKGROUND OF THE INVENTION

This invention relates generally to imaging systems, and more particularly to imaging systems that use a retractor.

Some imaging systems such as nuclear medicine imaging systems having gamma cameras use a retractor as a transmission system to transmit power, signals and data between the imaging detectors and electronics used for processing, control and power. The retractor may also be referred to as a cable guidance system and allows a limited rotation span. For example, the rotor or rotating portion upon which the imaging detectors are mounted typically may be rotated more than one, but less than two full rotations in one or both of the clockwise (CW) and counter-clockwise (CCW) directions from a zero position. In contrast, a slip ring, such as those used by computed tomography (CT) and some gamma camera systems, allow unlimited rotations in both the CW and CCW directions.

Electronics track the rotating portion during normal use, such as by receiving rotation input from an absolute encoder, potentiometer, tooth wheel and flag and/or encoder combination, and the like. An angular read-out on a display and/or a warning when nearing the end of travel may be provided. End of travel microswitches have also been used to try to prevent the system from reaching or exceeding a travel limit. Mechanical devices such as hard stops have been used, but cannot safely stop heavy modern imaging detectors and may not be easily positioned to stop rotation at a position less than two full revolutions. If the tracking or corresponding display fails, such as during a power outage or computer or other component malfunction, an operator may not know if the retractor is nearing the end of travel. Moving the rotating portion beyond the end of travel, such as manually or by driving with a motor, may cause severe damage to the system. Specifically, the retractor may be damaged if the rotating portion travels beyond the designed travel limit.

BRIEF DESCRIPTION OF THE INVENTION

In one embodiment, a rotating imaging system has a rotating portion that is configured to rotate about a central axis. A tilt gauge has a housing mounted to the rotating portion and a gravity influenced flag with a free end configured to move separately with respect to the housing. The tilt gauge is configured to provide a visual indication of a rotational position of the rotating portion.

In another embodiment, a tilt gauge for use with a rotating imaging system has a housing comprising a base. Sides extend outwardly from the base. A gravity influenced flag is attached at one end to the base and has a free end configured to move separately with respect to the housing to provide a visual indication of a rotational position of the housing with respect to a zero degree position of rotation. A substantially transparent cover is attached to the sides and the flag is positioned between the base and the cover.

In yet another embodiment a rotating imaging system comprises a rotating portion, a retractor and a tilt gauge. The rotating portion is configured to rotate about a central axis. The retractor is mounted to the rotating portion and is configured to rotate at least one full revolution. The tilt gauge has a housing mounted to the rotating portion and a gravity influenced flag with a free end configured to move separately with respect to the housing. A flag stopper is fixedly mounted to the housing and is configured to engage with the flag when the rotating portion is rotated a predetermined number of degrees in either clockwise (CW) or counter-clockwise (CCW) rotation directions.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
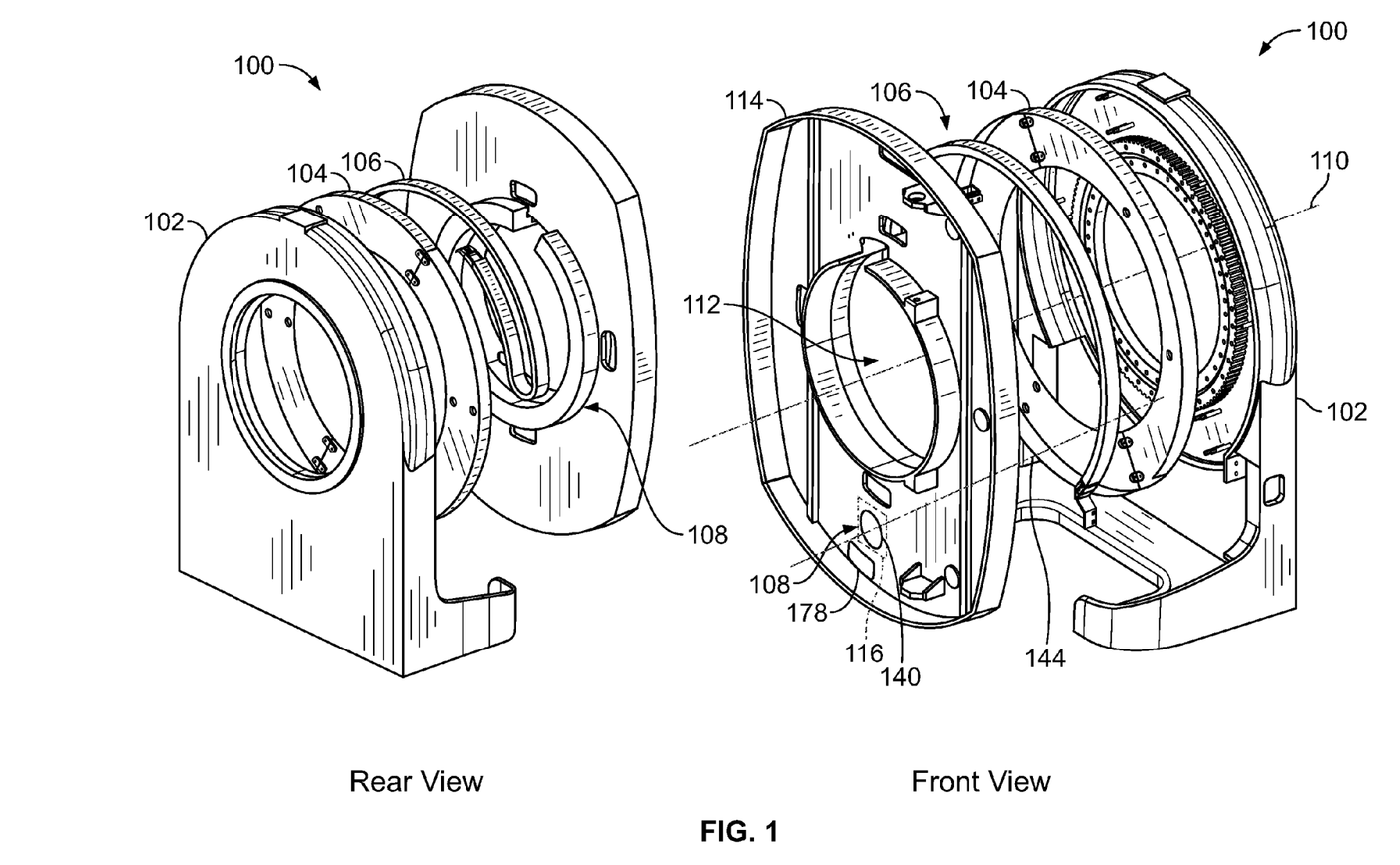
FIG. 1 illustrates exploded rear and front views of a gantry that may be used within a rotating imaging system formed in accordance with an embodiment of the present invention.

FIG. 1 illustrates exploded rear and front views of a gantry 100 that may be used within a rotating imaging system. A stator 102 is fixed to the floor or other structure, such as one or more rails (not shown). A retractor cage 104 is fixed to the stator 102 and is configured to hold a retractor 106. A rotor or rotating portion 108 is attached to and/or supported by the stator 102 such as through a slew bearing (not shown). The retractor 106 moves within the retractor cage 104 when the rotating portion 108 rotates. However, the retractor cage 104 is static and does not rotate.

The retractor 106 is a signal and power transmission system having a coiled transmission line that winds and unwinds as the rotating portion 108 rotates about a central axis 110 extending through an opening 112. The opening 112 is large enough to accommodate, for example, a patient on a pallet of a table (all not shown). The retractor 106 conveys at least one of power, image, data, and control signals between gamma camera imaging detector(s) (not shown) and a computer or other processor (not shown). In general, the retractor 106 may be capable of rotating about the central axis 110 for less than two full revolutions, thus having a rotation span or operating range of less than 720 degrees. In one embodiment, the retractor 106 rotates approximately one and a half revolutions in one direction, or about 540 degrees. In another embodiment, the retractor 106 may rotate more or less than one and a half revolutions in one direction while rotating less than one revolution in the opposite direction. In yet another embodiment, the retractor 106 may rotate more than two revolutions in at least one of the directions.

A tilt gauge 140 and a tilt sensor 178 are mounted on the rotating portion 108. As shown, the tilt gauge 140 and the tilt sensor 178 are mounted beneath an outer cover 114 that encloses at least a portion of the rotating portion 108. The cover 114 may have a viewing window 116 through which all or portions of the tilt gauge 140 may be viewed. For example, the viewing window 116 may be provided with a removable window cover, a transparent window cover, or may be a small open window. Alternatively, more than one small window may be provided, allowing an operator to view different portions of the tilt gauge 140. In another embodiment, no viewing window may be provided. In yet another embodiment, the tilt gauge 140 may be mounted on an outer surface of the cover 114. As the rotational portion 108 rotates, the tilt gauge 140 has a pendulum or flag (not shown) with a free end that rotates about a horizontal axis 144 that is parallel to the central axis 110 as discussed below.

Figure 2:
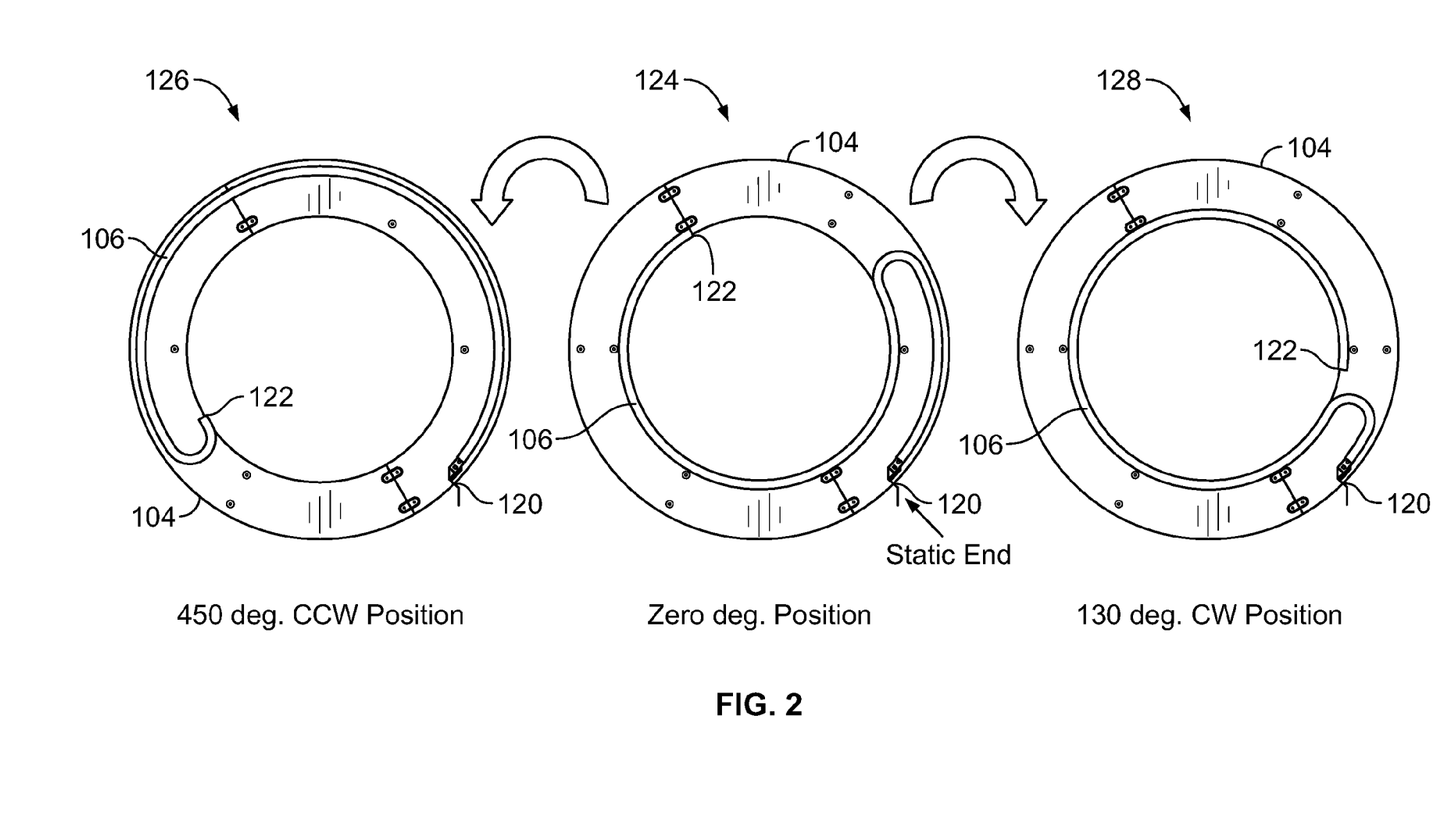
FIG. 2 illustrates an exemplary path of a retractor within a retractor cage as the rotating portion (shown in FIG. 1) is rotated in accordance with an embodiment of the present invention.

FIG. 2 illustrates an exemplary path of the retractor 106 within the retractor cage 104 as the rotating portion 108 (shown in FIG. 1) is rotated. The retractor 106 has a fixed or static end 120 attached to the retractor cage 104. Cables or other circuitry (not shown) may be interconnected at the static end 120 to convey signals between the retractor 106 and a processor, motion controller and/or other circuitry (not shown). A moving end 122 is not fixed to the retractor cage 104 and indicates the position of the retractor 106 as the retractor 106 is rotated. The position of the moving end 122 depends on the amount of clockwise (CW) or counter-clockwise (CCW) rotation. Cables or other circuitry (not shown) convey signals between the moving end 122 of the retractor 106 and the gamma camera imaging detector(s).

The retractor 106 may be coiled and/or folded within the retractor cage 104 at a zero degree position 124. The retractor 106 is also shown in a 450 degree CCW position 126. In this example, the maximum rotation in the CCW direction is 450 degrees. If the retractor 106 is rotated further than 450 degrees in the CCW direction, damage to the retractor 106 and/or other components may result. The 450 degree rotation is slightly less than one and a half full rotations in the CCW direction. However, it should be understood that the retractor 106 may be configured to rotate more or less than 450 degrees in the CCW direction.

The retractor 106 is further shown in a 130 degree CW position 128. In this example, the maximum rotation in the CW direction is 130 degrees, and if the retractor 106 is rotated further in the CW direction, damage may result. As with the CCW direction, the retractor 106 may be configured to rotate greater or lesser distances than 130 degrees in the CW direction.

In the illustrated embodiment, the total maximum rotation range of the retractor 106 is 580 degrees. In another embodiment, the retractor 106 may be configured to rotate further in the CW direction, such as 450 degrees, while rotating less than one full rotation in the CCW direction. In yet another embodiment, the retractor 106 may be configured to rotate approximately one full rotation in both CW and CCW directions.

Figure 3:
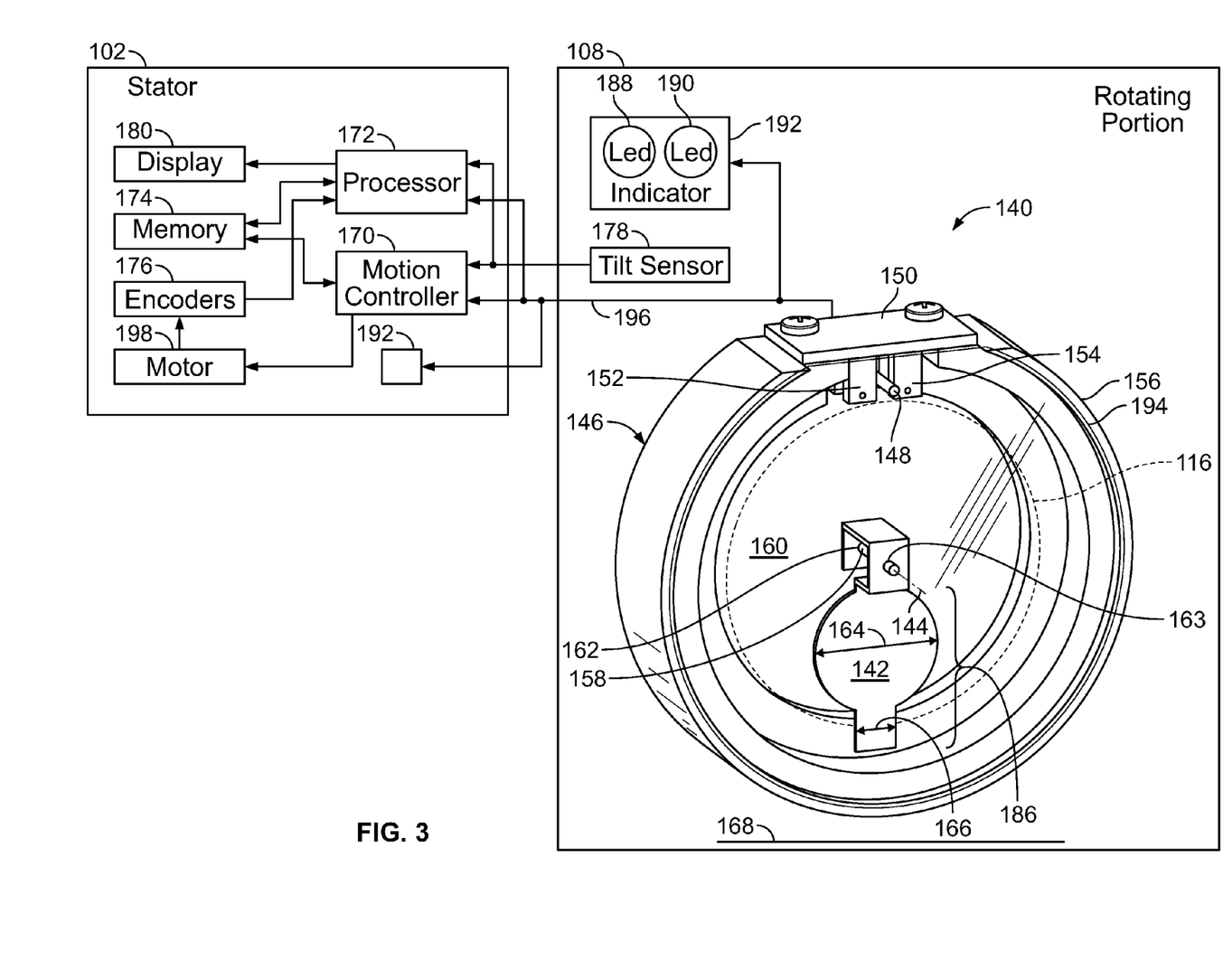
FIG. 3 illustrates a tilt gauge formed in accordance with an embodiment of the present invention that may be mounted on the rotating portion to visually indicate the rotational position of the rotating portion.

FIG. 3 illustrates the tilt gauge 140 that may be mounted on or beneath the outer cover 114 (as shown in FIG. 1) of the rotating portion 108. If the tilt gauge 140 is mounted on an outer surface of the outer cover 114 or the viewing window(s) 116 are provided, the tilt gauge 140 provides a visual indication of the rotational position of the rotating portion 108 to an operator. The tilt gauge 140 has a housing 146 with a back wall 160 that is mounted to the rotating portion 108 or the outer cover 114 with any suitable fastening means, such as with glue, adhesive, one or more screws and the like.

The tilt gauge 140 provides a visual output regardless of the availability of power, easily allowing the operator to determine in what direction or directions the rotating portion 108 may be safely rotated. Also, a technical effect of at least one embodiment is that during operation and upon system power-up, the tilt gauge 140 may provide a simple digital output that may be combined with information from a tilt sensor 178 to identify whether the rotating portion 108 may be nearing the end of travel, such as by identifying when the rotating portion 108 has been rotated beyond one full revolution. The tilt gauge 140 is not connected to any mechanical transmission, such as gears, belts, or tooth wheels, and does not require calibration or adjustment after service to any other components.

The tilt gauge 140 has a pendulum or flag 142 with a free end 186 that rotates about the horizontal axis 144. The term flag is used to indicate a physical structure, and thus the flag 142 may be made of a metal, plastic, composite, or other suitable material. A pin 158 may protrude from the back wall 160 of the housing 146 and may extend through one or more holes 162 and 163 in the flag 142 to attach the flag 142 to the back wall 160 at one end. The flag 142 is gravity influenced and freely rotates about the pin 158. It should be understood that other fixtures may be used to attach the flag 142 to the housing 146 while allowing the flag 142 to freely rotate about the axis 144. The flag 142 may be formed having a wider center portion 164 and a narrower portion 166 extending away from the pin 158. Other shapes may be used, such as, but not limited to, forming the flag 142 as a rectangle or a cylinder.

The flag 142 and the back wall 160 of the housing 146 may be provided in different colors. For example, the flag 142 may be a light, bright or reflective color or finish, while the back wall 160 is a contrasting or relatively darker color. The difference in color enhances the ability of the operator to accurately see the position of the flag 142. When a smaller viewing window 116 is used, such as one that does not allow the entire tilt gauge 140 to be viewed, the operator may determine the rotational position of the rotating portion 108 depending upon whether the flag 142 is visible or not.

In FIG. 3, the tilt gauge 140 is indicated in the zero degree position with the flag 142 pointing down to the floor or ground 168. A flag stopper 148 and sensor assembly 150 are mounted on the housing 146, and are positioned opposite the flag 142 when the tilt gauge 140 is at the zero degree position. The flag stopper 148 restricts the gravitational motion of the flag 142 when the rotating portion 108 rotates far enough in either the CW or CCW direction. The sensor assembly 150 has a CCW direction sensor 152 and a CW direction sensor 154 mounted on either side of the flag stopper 148. The sensors 152 and 154 may be, for example, optocouplers, pairing a light source such as a light emitting photo-diode with a photosensitive detector, ultrasound-based sensors, or any other sensor that detects the presence and absence of the flag 142 within a small area, e.g. predetermined area.

A substantially transparent cover 194 may be mounted on an outer edge 156 of the housing 146 to prevent dirt, debris, air currents and/or other environmental factors from interfering with the operation of the flag 142 and the sensors 152 and 154. The cover 194 may be formed from a plastic, plastic composite, or any other suitable material that has sufficient transparency to allow an operator to view the position of the flag 142.

When one of the sensors 152 and 154 senses the presence of the flag 142, which in the case of optocouplers may be by sensing a lack of light transmission, the sensor assembly 150 transmits information that may be used to determine the position of the rotating portion 108, such as whether the rotating portion 108 is rotated beyond a predetermined position, is within a predetermined range, or may be nearing the end of travel. The position information may be transmitted to a gantry motion controller 170 and/or a processor 172 by a cable or line 196, and may be stored in a memory 174. By way of example, the line 196 may also provide power to the sensor assembly 150. In another embodiment, the line 196 may be a wireless transmission and a battery (not shown) may be used to provide power to the sensor assembly 150.

By way of example only, the motion controller 170, the processor 172, the memory and display 180 may be housed within or connected to the stator 102. The motion controller 170 provides input to motor 198, and the motor 198 responds by driving the rotating portion 108 in one of the CW and CCW directions at desired speeds, stopping or slowing the rotation of the rotating portion 108, and the like. Encoders 176 may receive input based on the motor 198 and provide an output to the processor 172, indicating the measured rotational angle of the rotating portion 108. It should be understood that other configurations may be used to drive the rotating portion 108 and electronically track the rotational angle. In addition, some components such as the display 180 and processor 172 may be provided within a processing station (not shown) that is positioned near the stator 102.

The tilt sensor 178 may also be mounted to, and rotates with, the rotating portion 108 and may or may not be visible to the operator. The tilt sensor 178 may measure tilt or rotation angles up to 360 degrees. Therefore, the tilt sensor 178 can determine what angle the rotating portion 108 is at with respect to the zero position, but cannot identify that a complete revolution has been accomplished in one direction and that the angular measurement is associated with a second rotation. In one embodiment, the motion controller 170 or processor 172 may combine the information from the tilt sensor 178 and the tilt gauge 140 to determine if more than one revolution has occurred. For example, if the tilt sensor 178 reflects a change from 359 degrees to 0 degrees and the flag 142 had been detected by one of the sensors 152 and 154 followed by the absence of detection of the flag 142, a full revolution has occurred.

The display 180 may be used to display the angular measurement measured by the tilt sensor 178 as well as an indication of the current number of rotations detected by the tilt gauge 140. For example, the display 180 may display an actual angular measurement that is greater than 360 degrees based on data received from both the tilt sensor 178 and the tilt gauge 140. The display 180 may include one or more of a monitor, display screen, light emitting diodes (LEDs) or other indicators. For example, if the retractor 106 is rotated and is nearing the end of travel, the display 180 may indicate a warning to the operator, such as with a particular graphic, a flashing warning message or indication, a flashing light, or by illuminating a light of a particular color, such as red or orange, and the like. In another embodiment, the processor 172 may cause a sound or audible warning to be generated when the retractor 106 nears the end of travel. In yet another embodiment, the sensor assembly 150 may cause an LED 188 and 190 within an indicator 192 to be illuminated whenever the corresponding sensor 152 and 154 detects the flag 142. The indicator 192 may be mounted on the rotating portion 108 or the stator 102, for example.

Figure 4:
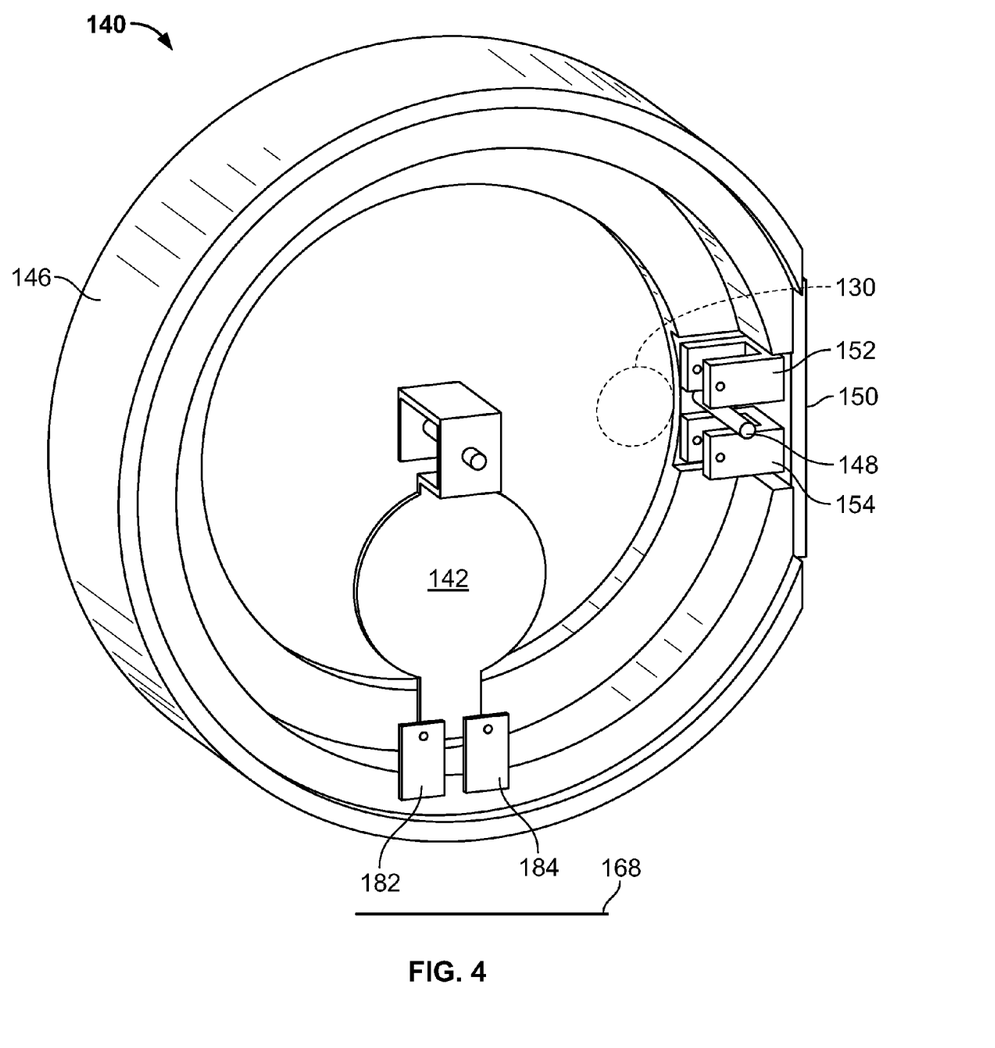
FIG. 4 illustrates the tilt gauge after being rotated approximately 90 degrees clockwise (CW) in accordance with an embodiment of the present invention.

FIG. 4 illustrates the tilt gauge 140 after being rotated approximately 90 degrees CW. The flag 142 is influenced by gravity and points to the ground 168. The flag stopper 148 and the sensor assembly 150 are positioned at approximately 90 degrees CW with respect to the zero degree position shown in FIG. 3. By simply viewing the tilt gauge 140, the operator knows that the rotating portion 108 has been rotated CW 90 degrees. The operator does not know, however, whether the rotating portion 108 has already been rotated a full rotation in the CW direction.

In one embodiment, the operator may view the tilt gauge 140 through a viewing window 130 that is smaller than the tilt gauge 140. The window 130 may be a small hole, one centimeter in diameter for example, in the outer cover 114. The viewing window 130 may be positioned proximate the sensor assembly 150. In FIG. 4, the operator would see only the back wall 160 of the tilt gauge through the window 130. In other embodiments as discussed above, the viewing window 116 may be larger to allow an operator to see more of the tilt gauge 140.

Additional sensors may be mounted on the housing 146 of the tilt gauge 140 to provide angular feedback based on detection of the flag 142. For example, one or more sensors 182 and 184 without an associated flag stopper may be mounted at a particular angle. As illustrated, the sensors 182 and 184 may be mounted at 90 degrees based on the zero degree position. Additional sensors may be mounted at different positions, such as at 90 and 270 degrees, mounted at a predetermined angular distance from each other, such as 10 degrees apart, and the like. If a single sensor 182 is used, the motion controller 170 will receive a signal when the flag 142 activates the sensor 182. If more than one sensor 182 and 184 is used, the motion controller 170 may determine in what direction the rotating portion 108 is being rotated based on which of the two sensors 182 and 184 transmits a signal first.

Figure 5:
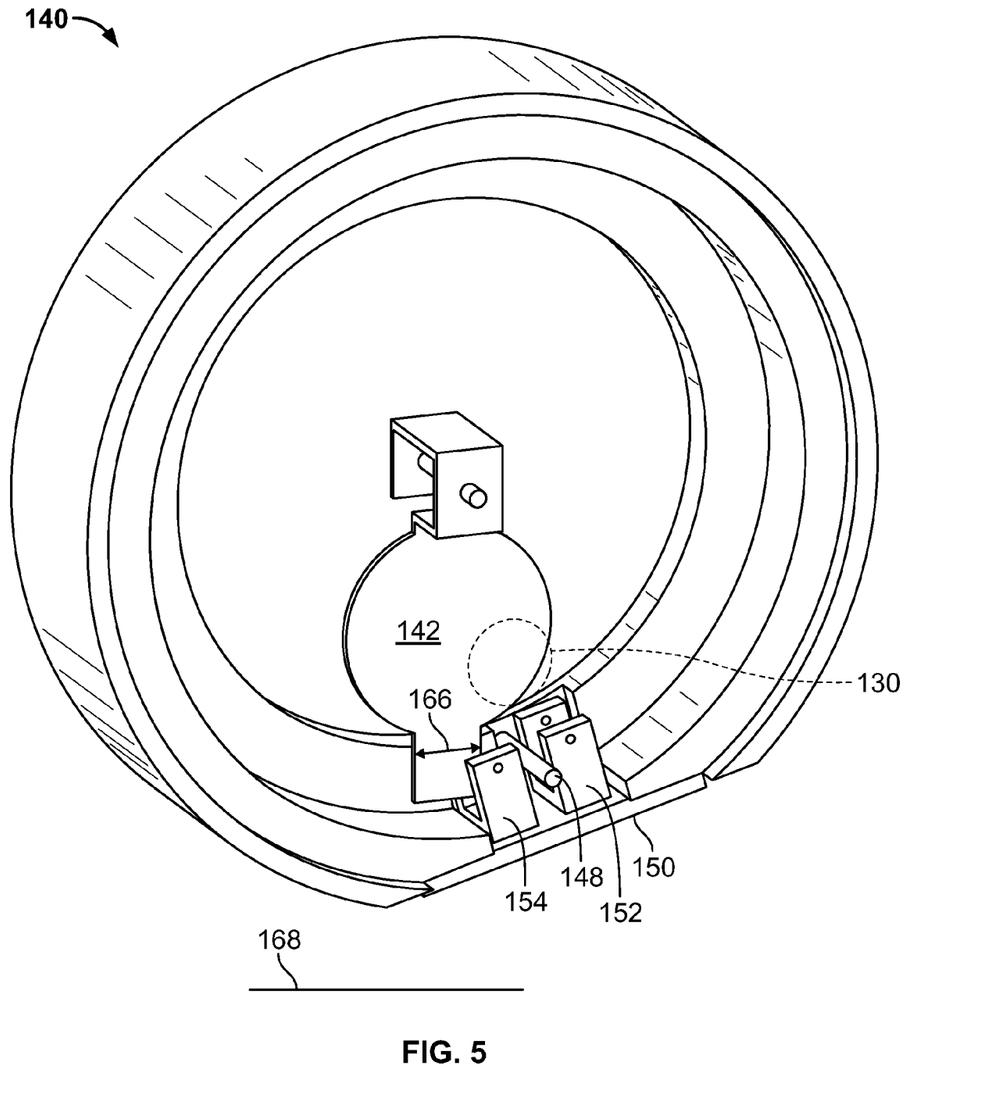
FIG. 5 illustrates the tilt gauge after being rotated approximately 165 degrees CW in accordance with an embodiment of the present invention.

FIG. 5 illustrates the tilt gauge 140 after being rotated approximately 165 degrees CW. The flag 142 is still influenced by gravity and points to the ground 168. The flag stopper 148 and the sensor assembly 150 are positioned at approximately 165 degrees CW with respect to the zero degree position shown in FIG. 3. The flag 142 does not touch the flag stopper 148, but does activate or otherwise cause the CW direction sensor 154 to send a signal to the motion controller 170 to indicate that the rotating portion 108 has been rotated a predetermined amount. For example, the narrower portion 166 of the flag 142 that activates the sensors 152 and 154 may be made wider such that the signal is generated prior to 165 degrees CW rotation. Also, the narrower portion 166 may be made narrower such that the signal is generated when the rotating portion 108 has been rotated more than 165 degrees CW, but less than 180 degrees CW. Therefore, the size and shape of the flag 142 may be modified and is not limited to the illustrated embodiment. However, the size of the flag 142 may be limited so that the sensors 152 and 154 do not detect the flag 142 prior to a predetermined angular position, such as prior to 90 degrees rotation.

In one embodiment, the operator can view at least a portion of the flag 142 through the viewing window 130. If the operator does not know the actual rotational position of the rotating portion 108, seeing the flag 142 may indicate a warning to the operator that the retractor 106 may be nearing the end of the rotation span.

Figure 6:
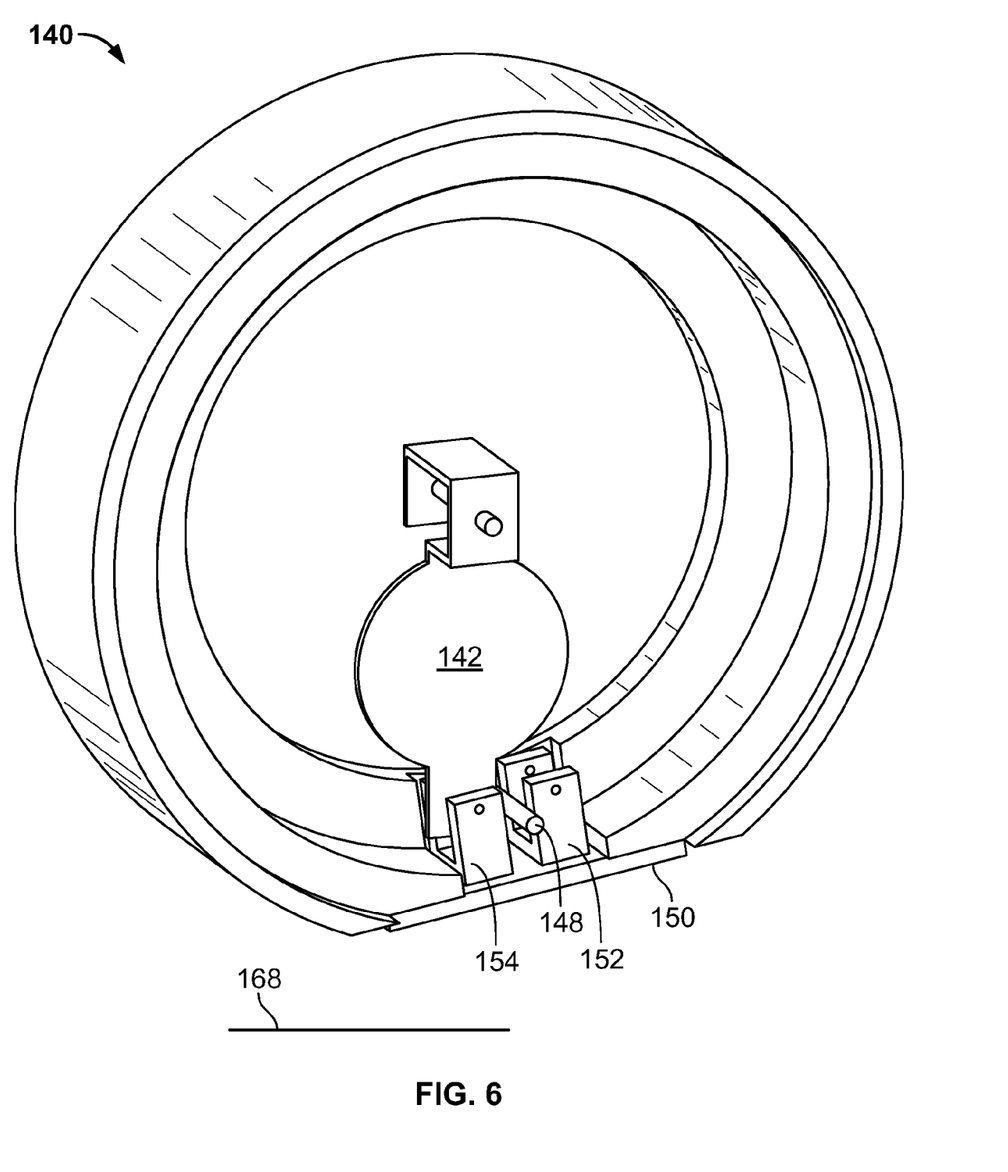
FIG. 6 illustrates the tilt gauge after being rotated approximately 172 degrees CW in accordance with an embodiment of the present invention.

FIG. 6 illustrates the tilt gauge 140 after being rotated approximately 172 degrees CW. The flag 142 is still pointing down to the ground 168 and the CW direction sensor 154 has been activated. At this position the flag 142 contacts the flag stopper 148. Therefore, the size of the flag 142 may also be based on a desired angular position at which to have the flag stopper 148 contact the flag 142. If further movement of the rotating portion 108 in the CW direction occurs, the flag 142 will be rotated or lifted by the force of the flag stopper 148. It should be understood that if the rotating portion 108 is rotated in the CCW direction, the CCW direction sensor 152 will be activated and the flag 142 will be lifted in the CCW direction.

Figure 7:
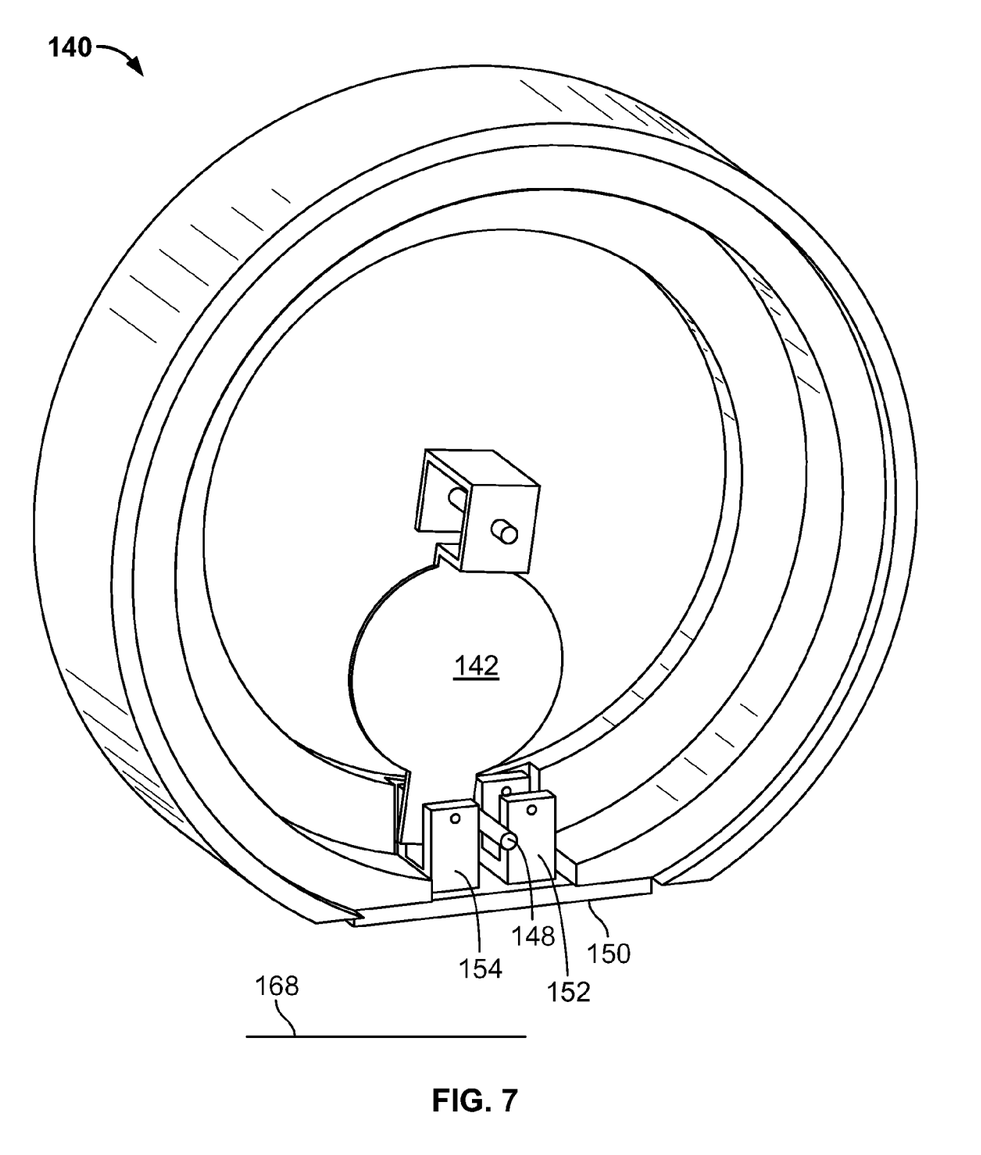
FIG. 7 illustrates the tilt gauge after being rotated approximately 180 degrees CW in accordance with an embodiment of the present invention.
Figure 8:
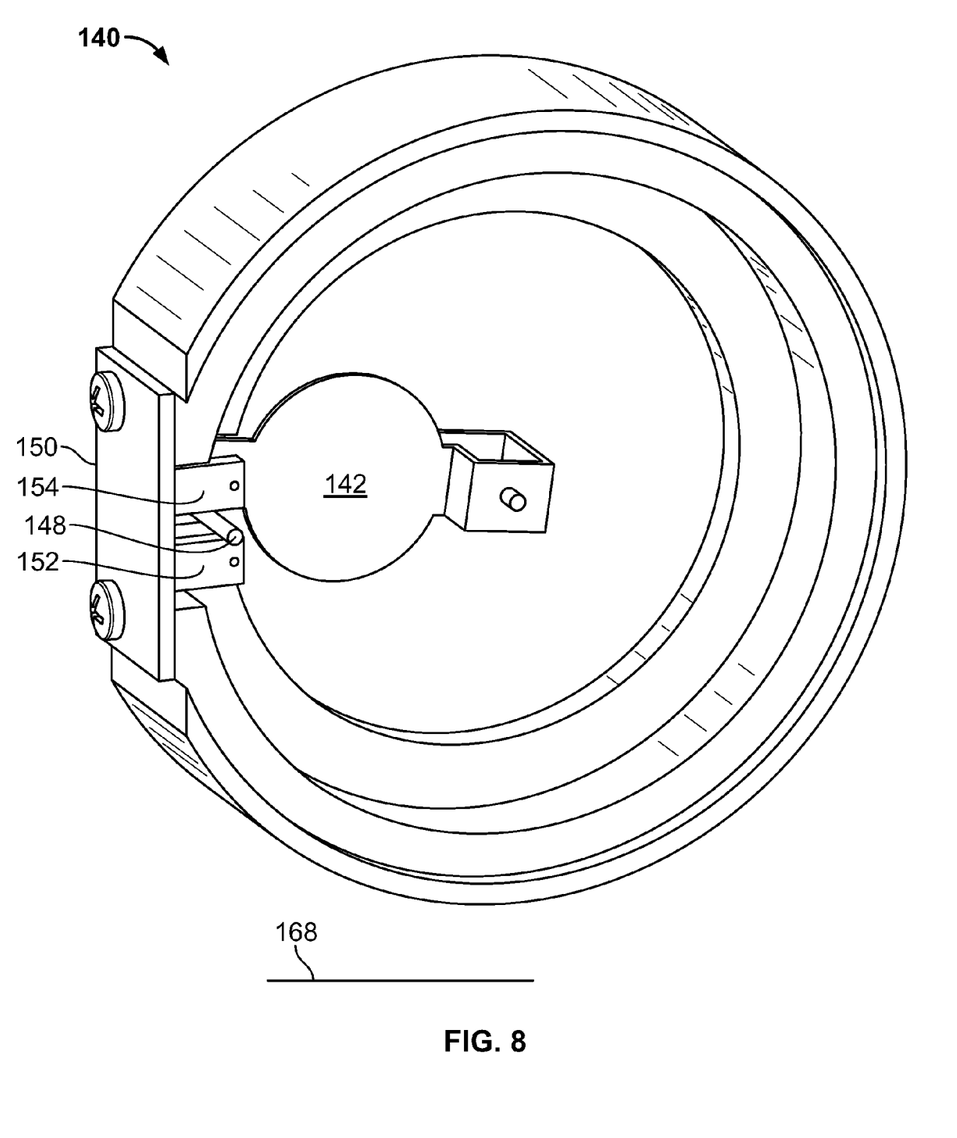
FIG. 8 illustrates the tilt gauge after being rotated approximately 270 degrees CW in accordance with an embodiment of the present invention.

FIGS. 7 and 8 illustrate the tilt gauge 140 after being rotated approximately 180 degrees CW and 270 degrees CW, respectively. The flag 142 continues to rotate with the flag stopper 148 and the CW direction sensor 154 continues to generate a signal indicating detection of the flag 142. When the rotating portion 108 is rotated approximately 360 degrees, or when the flag 142 has moved CW past a point wherein the flag 142 is perpendicular with respect to the ground 168, gravity causes the flag 142 to separate from the flag stopper 148 and to fall in the CW direction to point downwards at the ground 168.

The operator can look at the tilt gauge 140 at any time and determine if the retractor 106 is in a safe zone or potentially nearing the end of the rotational travel. For example, the power may be off or the actual angular data being displayed may be corrupt, which may be indicated by displaying an error message or an angular measurement on the display 180 that is obviously incorrect based on the physical position of the rotating portion 108.

Referring to FIG. 4, the operator may view the tilt gauge 140 and know that the retractor 106 is in a safe zone because the flag 142 is not in contact with the flag stopper 148. However, it may not be safe to rotate further in the CW direction because it is unknown whether the rotating portion 108 is rotated 90 or 450 degrees, or if the rotating portion 108 is nearing the end of travel in the CW direction. Referring to FIGS. 6, 7 and 8, the flag 142 is in contact with the flag stopper 148 and thus the operator knows that the retractor 106 may be nearing the angular end of travel. Therefore, it may not be safe to rotate the retractor 106 further in the CW direction. Rotation of the rotating portion 108 may be desired, for example, to move the imaging detector(s) into a particular position for servicing or to facilitate the removal of a patient. Therefore, if the actual rotation is not known and rotation of the rotating portion 108 causes the flag 142 to rise, the operator should stop and rotate the rotating portion 108 in the other direction.

Figure 9:
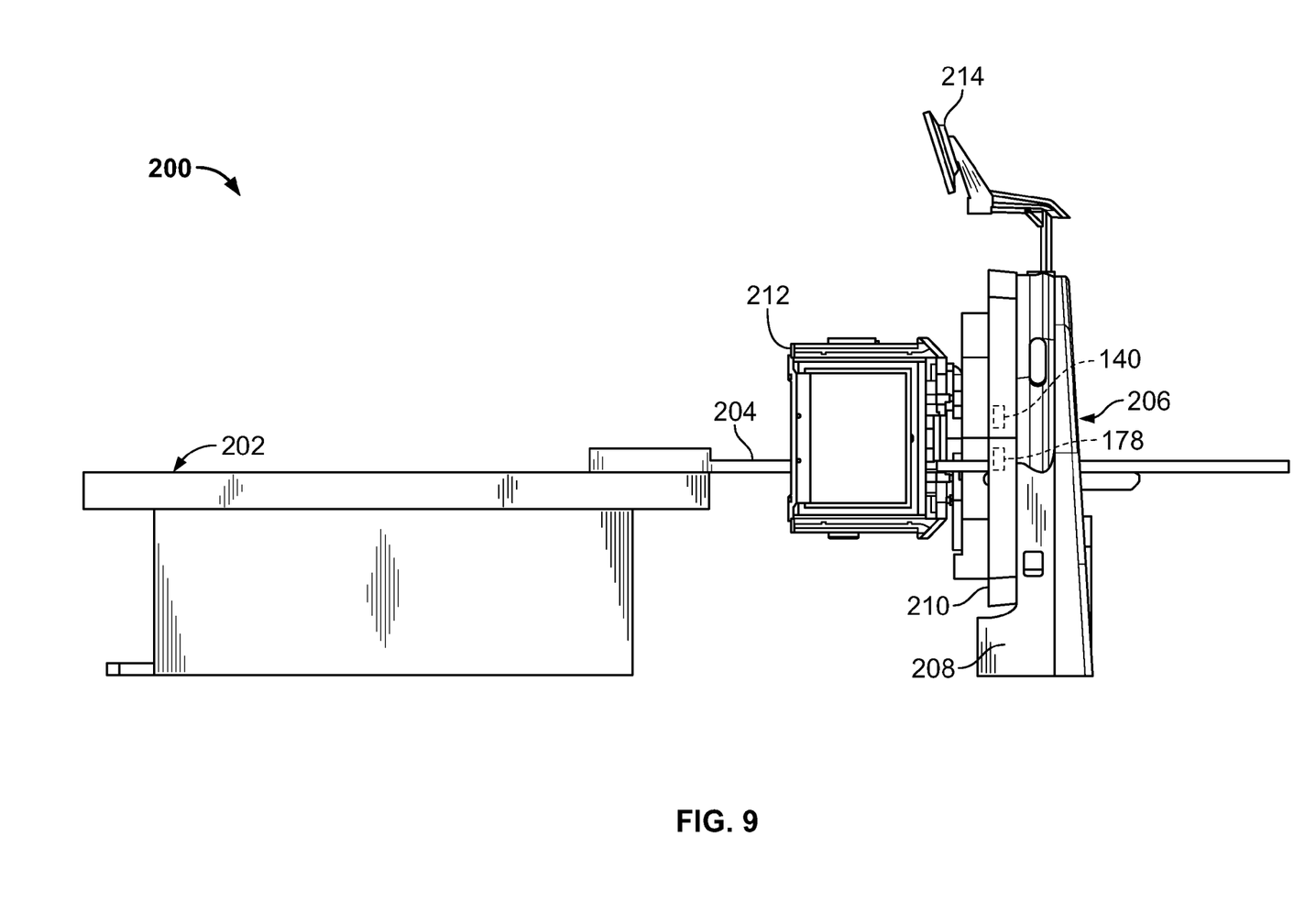
FIG. 9 illustrates an exemplary rotating imaging system that uses the tilt gauge formed in accordance with an embodiment of the present invention.

FIG. 9 illustrates an exemplary rotating imaging system 200 that uses the tilt gauge 140. In this example, the system 200 is a nuclear medicine (NM) imaging system that may be used for nuclear single photon emission computed tomography (SPECT) imaging. The imaging system 200 has a table 202 with a pallet 204 that extends through an opening 206, similar to the opening 112 of FIG. 1. A stator 208 supports a rotor or rotating portion 210 and is mounted to the floor. Two imaging detectors are mounted on the rotating portion 210, although only one imaging detector 212 is shown. The tilt gauge 140 is mounted on the rotating portion 210. The tilt gauge 140 may be positioned to facilitate viewing of the flag 142 from a direction along the central axis 110 (as shown in FIG. 1). Additionally, tilt sensor 178 may also be mounted to the rotating portion 210, but may not be visible to the operator. Display 214 may display diagnostic images as well as information identifying the rotational position of the rotating portion 210.

Figure 10:
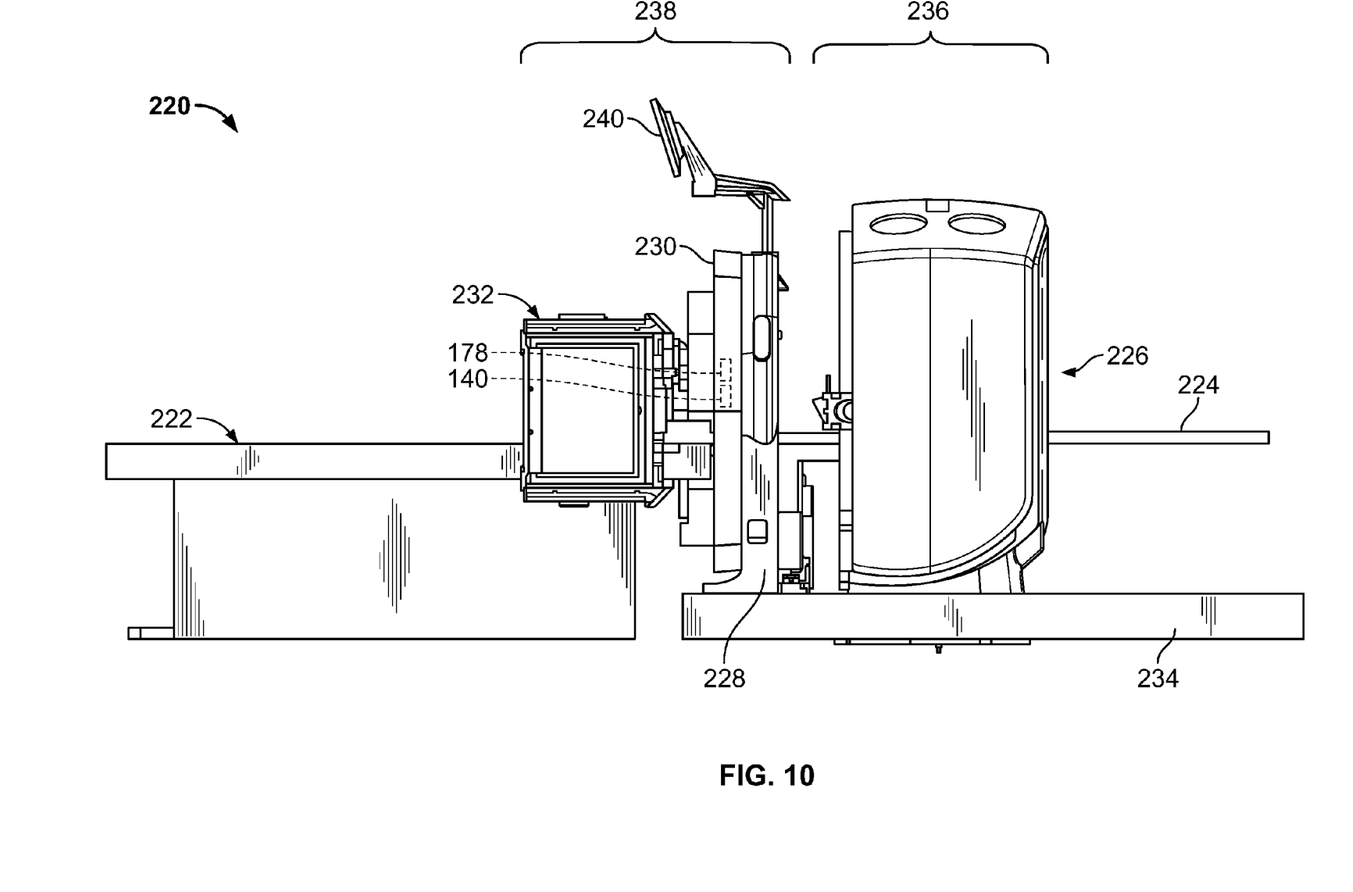
FIG. 10 illustrates another exemplary rotating imaging system that uses the tilt gauge formed in accordance with an embodiment of the present invention.

FIG. 10 illustrates another exemplary rotating imaging system 220 that uses the tilt gauge 140. In this example, the system 220 is a multi-modality imaging system 220. The system 220 has an NM imaging system 238 capable of SPECT imaging and a computed tomography (CT) imaging system 236. Although the CT imaging system 236 is shown, it should be understood that other types of imaging systems may be paired with the NM imaging system 238 or included within the multi-modality rotating imaging system 220. Also, the CT imaging system 236 may be a full diagnostic CT system having detailed resolution or a lower cost system used primarily for attenuation correction of the NM image data, anatomical registration and lower resolution imaging. As shown in FIG. 10, the imaging system 220 has a table 222 with a pallet 224 that extends through an opening 226. Also, a stator 228 supports a rotating portion 230 and at least one imaging detector 232. In this example, the stator 228 is mounted to at least one rail 234 and thus may be positioned with respect to the table 222. The CT system 236 is also mounted to the at least one rail 234. It should be understood that at least one of the stator 228 and the CT system 236 may instead be mounted to the floor.

The tilt gauge 140 is mounted to the rotating portion 230 as discussed above. The tilt sensor 178 is also mounted to the rotating portion 230. Display 240 displays rotational information received from the tilt gauge 140 and the tilt sensor 178, such as the rotational angle with respect to the zero degree position, an indication of absolute rotation angle with respect to the zero degree position, the number of revolutions in one direction and a warning indicating when the retractor 106 nears the end of travel in either of the CW or CCW directions. Although not shown, the indicator 192, as discussed previously in FIG. 3, may also be used within the systems 200 and 220 of FIGS. 9 and 10, respectively, to provide a visual indication to the operator.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A rotating imaging system, comprising:
   a rotating portion configured to rotate about a central axis;
   at least one medical imaging detector mounted to the rotating portion and configured to rotate about the central axis; and
   a tilt gauge comprising a housing mounted to the rotating portion, the tilt gauge further comprising a gravity influenced flag with a free end configured to move separately with respect to the housing due to gravity when the rotating portion is rotated about the central axis;
   wherein the tilt gauge further comprises at least one flag sensor configured to detect the flag as the rotating portion rotates, the at least one flag sensor further configured to generate a signal associated with at least one of clockwise (CW) rotation, counter-clockwise (CCW) rotation, or an angular measurement.

2. The system of claim 1, wherein the rotating portion is configured to rotate more than one revolution about the central axis, the system further comprising a tilt sensor mounted to the rotating portion, the tilt sensor configured to determine the rotational position of the rotating portion within a range of zero to 359 degrees, the system using the generated signal and the determined rotational position to determine an absolute position of the rotating portion.

3. The system of claim 1, wherein the tilt gauge further comprises a flag stopper fixedly mounted to the housing, the flag stopper configured to engage with and move the flag when the rotating portion is rotated beyond a predetermined number of degrees in either clockwise (CW) or counter-clockwise (CCW) directions.

4. The system of claim 1, further comprising:
   an outer cover configured to enclose at least a portion of the rotating portion; and
   a viewing window formed in the outer cover, the viewing window configured to allow at least a portion of the tilt gauge to be viewed from outside the outer cover.

5. The system of claim 1, wherein the housing of the tilt gauge comprises a base fixedly attached to the rotating portion and sides extending outwardly from the base, the tilt gauge further comprising a cover attached to the sides, the flag being positioned between the base and the cover.

6. The system of claim 1, wherein the tilt gauge further comprises:
   a flag stopper fixedly mounted to the housing;
   wherein the at least one flag sensor comprises first and second flag sensors positioned on opposite sides of the flag stopper, each of the first and second flag sensors configured to generate a signal when the flag is detected, the signal associated with at least one of a rotation direction or the rotational position of the rotating portion; and
   a motion controller configured to receive the signal and to determine if the rotating portion has completed a revolution in one direction.

7. The system of claim 1, wherein the system further comprises at least one indicator for indicating a rotation direction of the rotating portion based on a signal from the at least one flag sensor.

8. A tilt gauge for use with a rotating imaging system, the tilt gauge comprising:
   a housing including a cover;
   a gravity influenced flag in the housing, the flag comprising a solid structure having a free end that is configured to move separately with respect to the housing, due to gravity, to provide a visual indication of a rotational position of the housing when the housing is rotated about an external axis, the flag being visible through the cover, the housing having a fixed orientation with respect to the axis when rotated.

9. The tilt gauge of claim 8, further comprising a flag stopper fixedly mounted to the housing, the flag stopper configured to engage with and move the free end of the flag when the housing is rotated at least a predetermined number of degrees in a clockwise (CW) direction and also when the housing is rotated at least a predetermined number of degrees in a counter-clockwise (CCW) direction.

10. The tilt gauge of claim 8, further comprising at least one flag sensor fixedly mounted to the housing and configured to detect the flag as the housing rotates, the at least one flag sensor further configured to generate a signal associated with at least one of clockwise (CW) rotation, counter-clockwise (CCW) rotation, or an angular measurement with respect to a zero degree position.

11. The tilt gauge of claim 8, further comprising:
    a flag stopper fixedly mounted to the housing; and
    first and second flag sensors fixedly mounted to the housing on either side of the flag stopper, each of the first and second flag sensors configured to generate a signal when the flag is detected.

12. The tilt gauge of claim 8, further comprising a pin configured to attach the flag to the housing, the pin and the flag being rotatably attached such that the flag rotates within a plane that substantially coincides with a gravitational pull axis.

13. The tilt gauge of claim 8, wherein the housing includes a base and sides that extend from the base, the cover being attached to the sides, wherein the flag is positioned between the base and the cover.

14. The tilt gauge of claim 8, wherein the cover includes a viewing window, the window being located such that the flag is visible through the window for select rotational positions of the housing with respect to the external axis and not visible for other rotational positions of the housing with respect to the external axis.

15. A rotating imaging system, comprising:
    a rotating portion configured to rotate about a central axis;
    a retractor mounted to the rotating portion and configured to rotate at least one full revolution, the retractor including a transmission line configured to convey signals, the transmission line winding or unwinding as the rotating portion is rotated; and a tilt gauge comprising:
- a gravity influenced flag comprising a solid structure, the flag being coupled to the rotating portion and having a free end configured to rotate about a horizontal axis that extends parallel to the central axis; and
- a flag stopper coupled to and having a fixed position relative to the rotating portion, the flag stopper configured to engage with the flag when the rotating portion is rotated a predetermined number of degrees in either clockwise (CW) or counter-clockwise (CCW) rotation directions.

16. The system of claim 15, wherein the tilt gauge further comprises first and second flag sensors positioned on opposite sides of the flag stopper, each of the first and second flag sensors configured to generate a signal when the flag is detected.

17. The system of claim 15, wherein the tilt gauge further comprises at least one flag sensor configured to detect the flag as the rotating portion rotates, wherein the system further comprises at least one of (a) a display or (b) an indicator for indicating at least one of an angular measurement of the rotating portion, the CW or CCW rotation direction of the rotating portion, or a warning of an end of travel of the retractor based on a signal from the at least one flag sensor.

18. The system of claim 15, wherein the tilt gauge further comprises first and second flag sensors, each of the first and second flag sensors configured to generate a signal when the flag is detected, wherein the system further comprises a motion controller configured to receive the signal and to determine whether the retractor is nearing a maximum rotation based on the signal.

19. The system of claim 15, further comprising at least one medical imaging detector mounted to the rotating portion and configured to rotate about the central axis, the at least one medical imaging detector being communicatively coupled to the transmission line.

20. The system of claim 15, further comprising a housing mounted to the rotating portion, the flag stopper being fixedly mounted to the housing, the housing including a cover having a viewing window such that the flag is viewable through the cover.

21. A rotating imaging system, comprising:
- a rotating portion configured to rotate about a central axis that extends substantially perpendicular to a gravitational pull axis;
- a retractor mounted to the rotating portion and configured to rotate more than one full revolution, the retractor including a transmission line configured to convey signals, the transmission line winding or unwinding as the rotating portion is rotated; and
- a tilt gauge comprising:
  - an element stopper coupled to and having a fixed position relative to the rotating portion, the stopper configured to engage an element that moves about a horizontal axis that extends parallel to the central axis when the rotating portion is rotating about the central axis; and
  - first and second sensors positioned on opposite sides of the stopper, each of the first and second sensors configured to generate a signal when the element is detected.

* * * * *